(12) United States Patent
Yamashita

(10) Patent No.: US 11,284,857 B2
(45) Date of Patent: Mar. 29, 2022

(54) MEDICAL DEVICE

(71) Applicant: TERUMO KABUSHIKI KAISHA, Tokyo (JP)

(72) Inventor: Yasunori Yamashita, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 527 days.

(21) Appl. No.: 15/446,841

(22) Filed: Mar. 1, 2017

(65) Prior Publication Data

US 2017/0172541 A1   Jun. 22, 2017

Related U.S. Application Data

(63) Continuation of application No. PCT/JP2015/073033, filed on Aug. 17, 2015.

(30) Foreign Application Priority Data

Sep. 3, 2014 (JP) .............................. JP2014-178929

(51) Int. Cl.
*A61B 8/12* (2006.01)
*A61B 8/00* (2006.01)
(Continued)

(52) U.S. Cl.
CPC ................ *A61B 8/12* (2013.01); *A61B 8/445* (2013.01); *A61B 8/461* (2013.01); *A61B 1/01* (2013.01); *A61B 1/018* (2013.01)

(58) Field of Classification Search
CPC ......... A61B 8/4461; A61B 8/445; A61B 8/12; A61B 8/461; A61B 1/018; A61B 1/01
See application file for complete search history.

(56) References Cited

U.S. PATENT DOCUMENTS 5,372,138 A * 12/1994 Crowley ................ A61B 5/416
600/463
5,976,093 A    11/1999 Jang
(Continued)

FOREIGN PATENT DOCUMENTS

JP    2000-197603 A    7/2000
JP    2004-097286       4/2004
(Continued)

OTHER PUBLICATIONS

The extended European Search Report dated Apr. 5, 2018, by the European Patent Office in corresponding European Patent Application No. 15837680.6-1124. (7 pages).
(Continued)

*Primary Examiner* — Keith M Raymond
*Assistant Examiner* — Patrick M Mehl
(74) *Attorney, Agent, or Firm* — Buchanan Ingersoll & Rooney PC

(57) ABSTRACT

A medical device includes a sheath having a guide wire lumen allowing a guide wire to be inserted therein and an imaging core lumen configured to have an ultrasound transducer inserted therein that acquires image information inside a living body. The medical device includes a rotary shaft that is inserted into the imaging core lumen and is rotatable in order to transmit mechanical drive force to the ultrasound transducer. In the sheath, a circular portion having a constant radii of curvature of the imaging core lumen is formed on a side separated from the guide wire lumen, and a non-circular portion having distances from the center point of the circular portion to the inner surface of the imaging core lumen non-uniform and longer than the radius of the circular portion is formed in at least a part of a side close to the guide wire lumen.

16 Claims, 13 Drawing Sheets

(51) Int. Cl.
*A61B 1/018* (2006.01)
*A61B 1/01* (2006.01)

(56) References Cited

U.S. PATENT DOCUMENTS

| | | | |
|---|---|---|---|
| 6,290,668 B1 | 9/2001 | Gregory et al. | |
| 7,155,272 B2* | 12/2006 | Yamaguchi | A61B 8/12 600/425 |
| 7,329,223 B1* | 2/2008 | Ainsworth | A61B 5/0084 600/300 |
| 8,080,000 B2* | 12/2011 | Makower | A61B 1/00135 604/510 |
| 2005/0101870 A1 | 5/2005 | Yamaguchi et al. | |
| 2010/0121153 A1* | 5/2010 | To | A61B 10/06 600/214 |
| 2010/0249599 A1* | 9/2010 | Hastings | A61B 5/02007 600/459 |
| 2011/0021911 A1 | 1/2011 | Waters et al. | |
| 2011/0224650 A1* | 9/2011 | Itou | A61B 8/12 604/524 |
| 2012/0271174 A1* | 10/2012 | Iwahashi | A61B 5/0084 600/467 |
| 2013/0211324 A1* | 8/2013 | Voss | A61M 25/04 604/104 |
| 2013/0225995 A1 | 8/2013 | Hashiguchi et al. | |
| 2013/0331706 A1* | 12/2013 | Hossack | A61B 8/445 600/467 |
| 2014/0243873 A1* | 8/2014 | Franklin | A61M 25/0097 606/194 |

FOREIGN PATENT DOCUMENTS

| | | |
|---|---|---|
| JP | 2008-537693 A | 9/2008 |
| JP | 2011-045534 A | 3/2011 |
| WO | WO 2006-105353 A | 10/2006 |
| WO | WO 2013/062039 A1 | 5/2013 |

OTHER PUBLICATIONS

International Search Report (PCT/ISA/210) dated Oct. 27, 2015, by the Japanese Patent Office as the International Searching Authority for International Application No. PCT/JP2015/073033.

Written Opinion (PCT/ISA/237) dated Oct. 27, 2015, by the Japanese Patent Office as the International Searching Authority for International Application No. PCT/JP2015/073033.

* cited by examiner

MEDICAL DEVICE

CROSS-REFERENCES TO RELATED APPLICATIONS

This application is a continuation of International Application No. PCT/JP2015/073033 filed on Aug. 17, 2015, which claims priority to Japanese Application number 2014-178929, filed on Sep. 3, 2014, the entire contents of both being incorporated herein by reference.

TECHNICAL FIELD

The present invention relates to a medical device having an, image-capturing function.

BACKGROUND ART

In the related art, image diagnosis has been performed by inserting a medical device having an image-capturing function into a blood vessel such as the coronary artery of the heart, or a lumen such as the bile duct.

As a medical device having an image-capturing function, an intravascular ultrasound (IVUS) diagnostic apparatus can be exemplified. Generally, in the intravascular ultrasound diagnostic apparatus, an ultrasound detector (probe) internally equipped with an ultrasound transducer is rotatably disposed inside an elongated pipe body. In the pipe body, an observation unit lumen rotatably accommodating the probe is formed, and a guide wire lumen is formed allowing a guide wire for guiding the image diagnostic apparatus to a target position to be inserted therein. The guide wire which has been inserted to a location near the target position inside a blood vessel in advance is inserted into the guide wire lumen, and the probe is disposed at the target position by moving the pipe body along the guide wire. Thereafter, after the probe performs radial scanning inside the pipe body and a reflected wave (ultrasound wave echo) reflected by biological tissue is received by the same probe processing such as amplification, wave detection or the like is executed. Accordingly, a cross-sectional image of a blood vessel can be visualized based on the intensity of the generated ultrasound wave echo.

In the intravascular ultrasound diagnostic apparatus, in order to minimize insertion of the intravascular ultrasound diagnostic apparatus in to a living body much as possible, it is desirable that the probe is provided at a distal end of the intravascular ultrasound diagnostic apparatus as far as possible. Therefore, the guide wire lumen provided on a distal side closer than the probe is inevitably required to have a short length in the axial line direction. However, when the guide wire lumen is shortened, operability is deteriorated, and a phenomenon in which the intravascular ultrasound diagnostic apparatus does not advance along the guide wire as intended is likely to occur. Therefore, Japanese Patent No. JP-A-2004-97286 discloses an intravascular ultrasound diagnostic apparatus which a first guide wire lumen is provided on the distal side closer than the probe and a second guide wire lumen is provided on a proximal side closer than the probe. When two guide wire lumens are provided in the intravascular ultra sound diagnostic apparatus, the intravascular ultrasound diagnostic apparatus can be stably moved along the guide wire, and thus, operability is improved.

However, in a case where a mechanism (medium drawing mechanism) of moving a probe in an axial line direction inside an observation unit lumen is provided and the probe acquires an image, even at a position side by side with a second guide wire lumen, the thickness of a pipe body becomes thick at the position where the observation unit lumen and the second guide wire lumen are provided. Therefore, a missing image is likely to occur due to ultrasound wave attenuation in a wide-range angle.

SUMMARY

The disclosure herein has been made in order to solve the aforementioned problems, and to provide a medical device which can acquire an image throughout a wide range as much as possible.

The disclosure is directed to a medical device provided with a pipe body having a guide wire lumen allowing a guide wire to be inserted therein and an observation unit lumen having an observation unit that acquires image information inside a living body to be inserted therein. The medical device includes a rotary shaft that is inserted into the observation unit lumen and is rotatable in order to transmit mechanical drive force to the observation unit. In the pipe body, a circular portion having uniform radii of curvature of the observation unit lumen is formed on a side separated from the guide wire lumen, and a non-circular portion having distances from the center point of the circular portion to the inner surface of the observation unit lumen non-uniform and longer than the radius of the circular portion is formed in at least a part of a side close to the guide wire lumen.

In the medical device having the above-described configuration, the non-circular portion having an inner diameter of the observation unit lumen greater than that of the circular portion is formed in at least a part of the side close to the guide wire lumen. Therefore, the thickness of a catheter at the non-circular portion becomes thin, and a missing image occurring due to attenuation of an ultrasound wave, light, and the like is reduced as much as possible. Thus, an image can be acquired throughout a wide range as much as possible.

When the pipe body includes a support portion having an inner diameter equal to the inner diameter of the circular portion in at least a part of the side close to the guide wire lumen, the support portion can stably support the observation unit and the rotary shaft during rotation, and thus, a favorable image can be acquired.

When the support portion has curvature equal to the curvature of the circular portion, the observation unit and the rotary shaft can be more stably supported during rotation. Thus, a favorable image can be acquired.

When the thicknesses of the non-circular portion are formed so as to be constant or thin toward the guide wire lumen side, attenuation of an ultrasound wave, light, and the like can be easily anticipated. Thus, an image can be easily corrected.

When a surface configuring the outside of the non-circular portion on the outer circumferential surface of the pipe body is formed so as to be a plane, high strength can, be obtained while the pipe body is minimized in size as much as possible and blood and the like are unlikely to be accumulated on the outer circumferential surface of the pipe body. Thus, a thrombus and the like can be suppressed from adhering thereto.

When the observation unit is an ultrasound transducer, even though the observation unit lumen needs to be filled with liquid, the non-circular portion having a significant inner diameter is formed and the volume of the observation unit lumen increases. Thus, the liquid can replace the inside of the observation unit lumen at lower pressure.

DETAILED DESCRIPTION

Hereinafter, with reference to the drawings, an exemplary embodiment of the disclosure will be described. Note that, for the convenience of description, there are cases where the dimensional ratios of the drawings are exaggerated and are different from the actual ratios.

Figure 1:
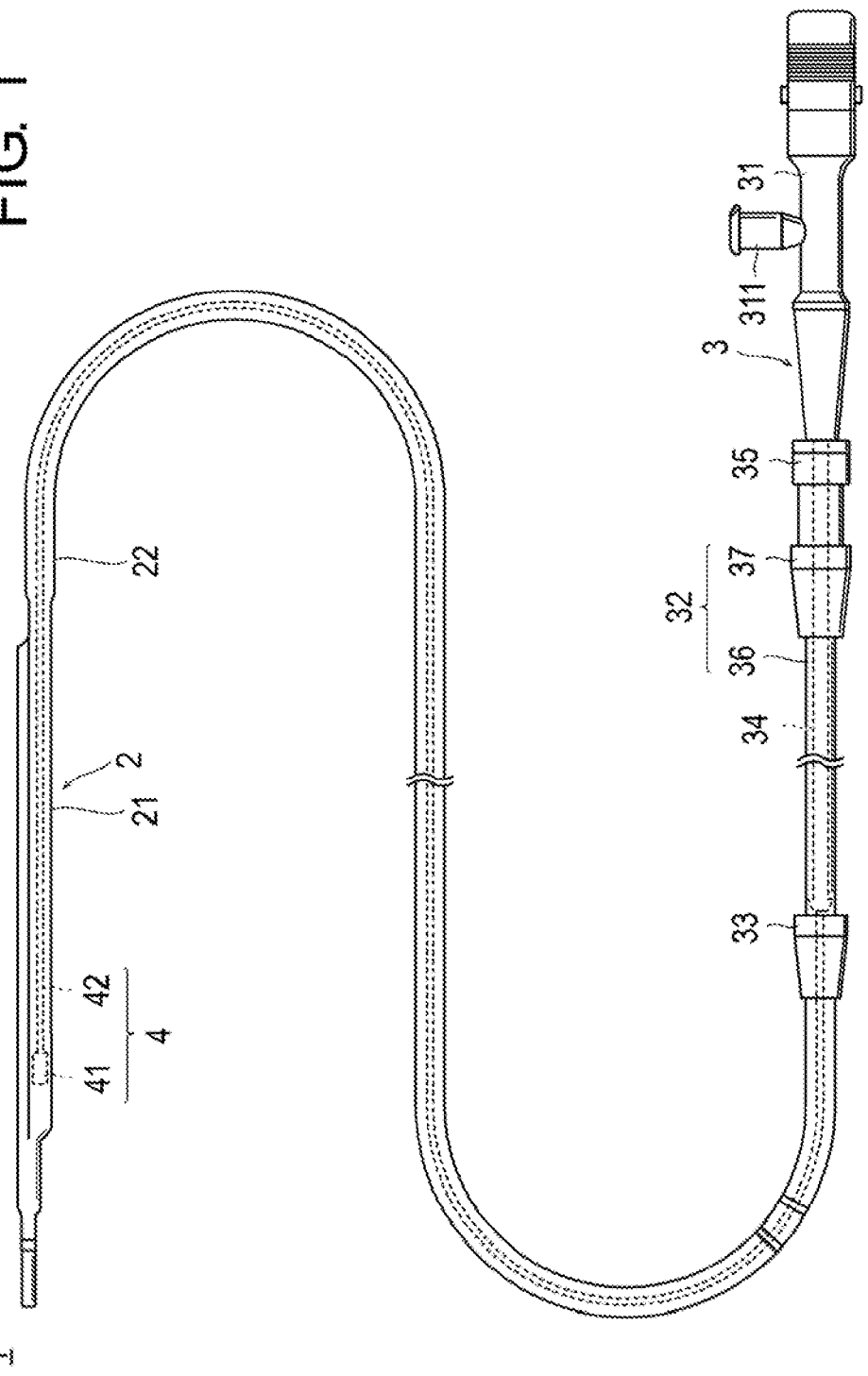
FIG. 1 is a plan view illustrating a medical device according to an exemplary embodiment of the disclosure.
Figure 2:
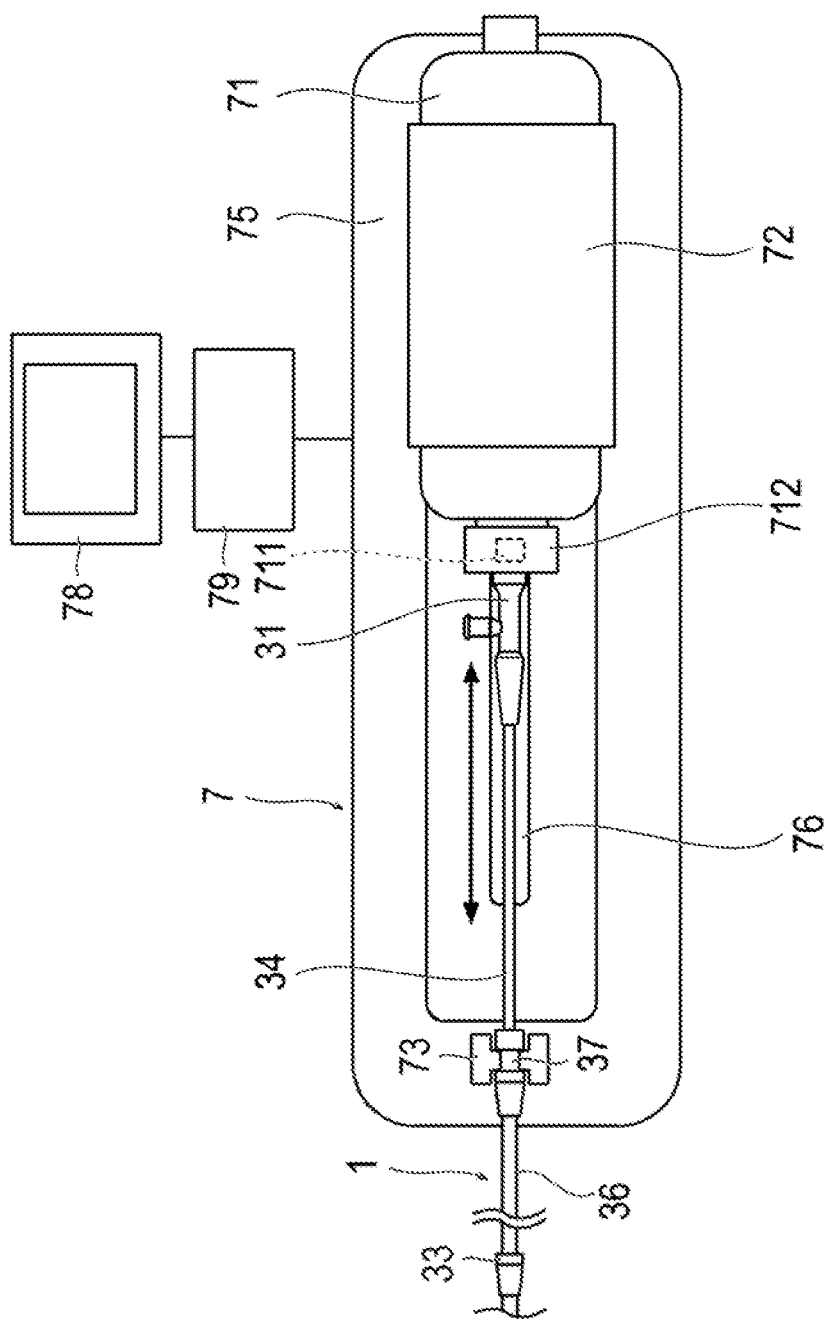
FIG. 2 is a plan view illustrating an intraluminal diagnosis system.

As illustrated in FIGS. 1 and 2, a medical device according to an exemplary embodiment herein is an ultrasound catheter 1 which internally accommodates an imaging core 4 for performing ultrasound diagnosis and which is inserted into a biological lumen. The ultrasound catheter 1 is connected to an external drive apparatus 7 which holds the ultrasound catheter 1 and drives the imaging core 4, and is thereby used to perform diagnosis mainly inside a blood vessel. Note that, in the disclosure herein, a side inserted into the lumen of a living body will be referred to as "distal end" or "distal side". An operating hand-side will be referred to as "proximal end" or "proximal side".

The ultrasound catheter 1 is provided with a sheath 2 which is inserted into the lumen, the imaging core 4 which transmits and receives ultrasound waves toward intraluminal tissue, and an operation unit 3 which is positioned on the proximal side closer than the sheath 2 and into which the imaging core 4 extends.

Figure 3:
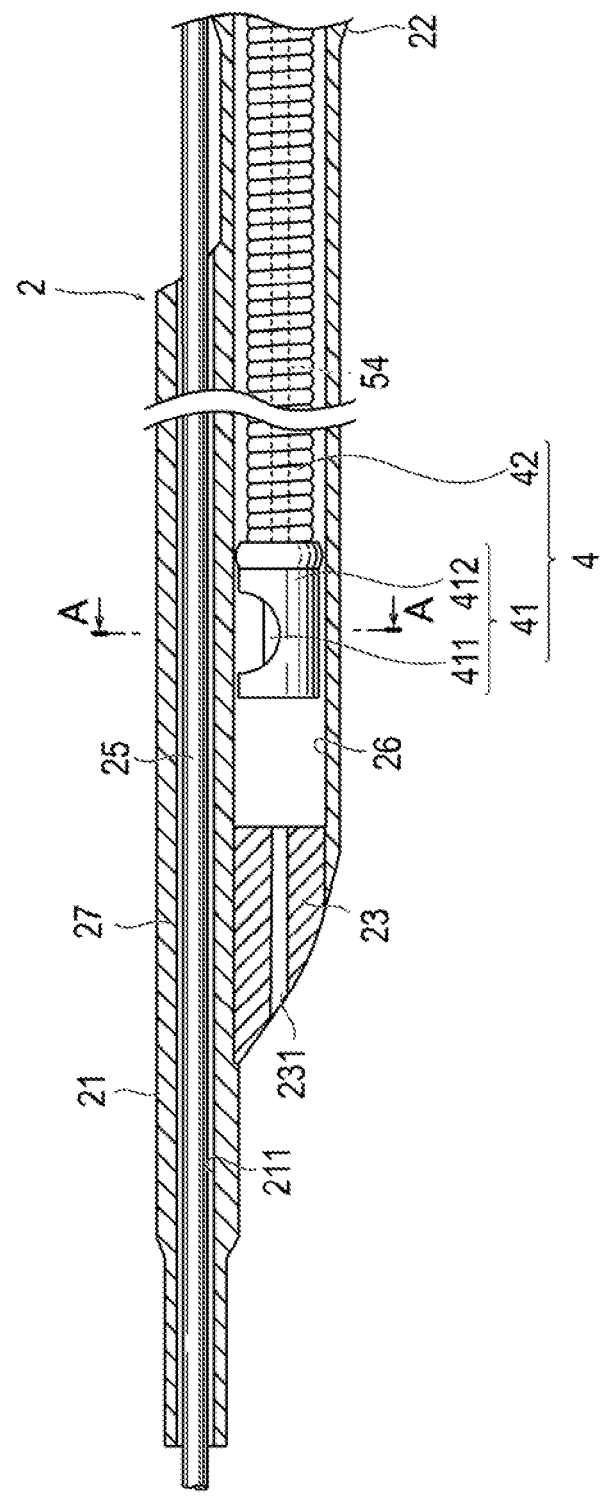
FIG. 3 is a cross-sectional, view in a longitudinal direction illustrating a distal portion of the medical device shown in FIG. 1.

As illustrated in FIG. 3, the sheath 2 has a sheath distal portion 21, a sheath main body portion 22 which is formed on the proximal side of the sheath distal portion 21, and a filling liquid in-out path member 23.

An imaging core lumen 26 (observation unit lumen) is formed in the sheath distal portion 21 and the sheath main body portion 22 which communicate with each other. The imaging core lumen 26 is a hollow passage formed inside the sheath 2.

The imaging core 4 is disposed inside the imaging core lumen 26 so as to be slidable in the axial line direction of the sheath 2. The imaging core 4 is provided with a transducer unit 41 which transmits and receives ultrasound waves from the inside of the lumen to biological tissue, and a rotary shaft 42 to which the transducer unit 41 is rotatably attached at the distal end thereof. The transducer unit 41 is configured to have an ultrasound transducer 411 (observation unit) which transmits and receives ultrasound waves, and a housing 412 which stores the ultrasound transducer 411.

A guide wire lumen 211 that is a passage for allowing a guide wire 25 to pass through the guide wire lumen 211 is formed at the sheath distal portion 21. The guide wire lumen 211 is open at the outermost distal end of the sheath distal portion 21 and is open at a location near a proximal portion of the sheath distal portion 21, that is, a location near a distal portion of the sheath main body portion 22. With the guide wire lumen 211 and the imaging core lumen 26 thus formed, the sheath distal portion 21 has a shape elongated in a direction in which the guide wire lumen 211 and the imaging core lumen 26 are arranged side by side in a cross section orthogonal to a longitudinal direction.

Figure 4:
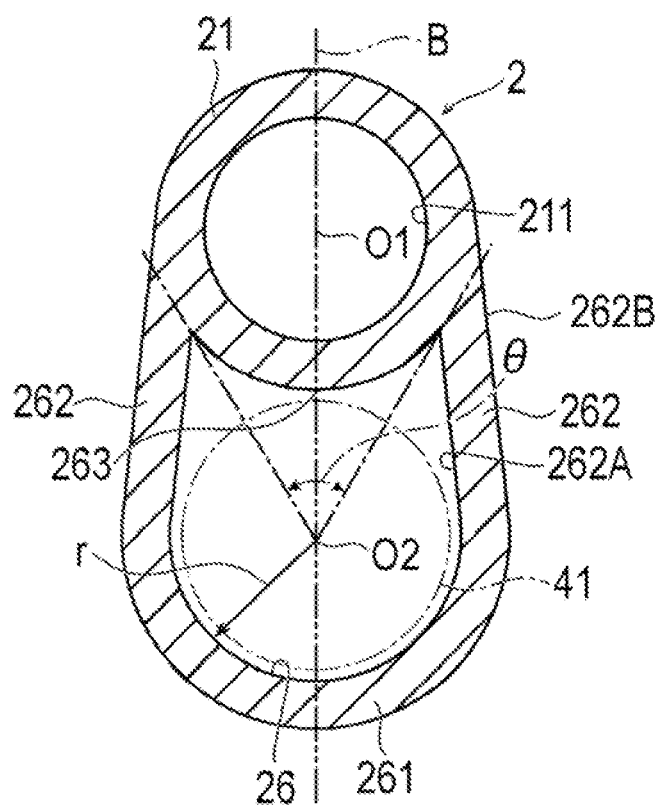
FIG. 4 is a cross-sectional view taken along line A-A in FIG. 3.

As illustrated in FIG. 4, at a portion where both the guide wire lumen 211 and the imaging core lumen 26 are formed side by side in the sheath distal portion 21, both a circular portion 261, having uniform radii of curvature of the imaging core lumen 26 and having constant inner diameters, r, and a non-circular portion 262, having distances from the center point (axis center O2) of the circular portion 261 to the inner surface of the imaging core lumen 26 being non-uniform and longer than the inner diameter r of the circular portion 261, are formed around the imaging core lumen 26. In a cross section orthogonal to the longitudinal direction of the sheath distal portion 21, the circular portion 261 is formed on a side separated or spaced from the guide wire lumen 211. In the cross section orthogonal to the longitudinal direction of the sheath distal portion 21, the non-circular portion 262 is formed in at least a part of a side close to the guide wire lumen 211. In the exemplary embodiment, in the cross section orthogonal to the longitudinal direction of the sheath distal portion 21, the non-circular portion 262 is symmetrically formed on both sides with respect to a reference surface B passing through an axis center O1 of the guide wire lumen 211 and an axis center O2 of the imaging core lumen 26. At least a part of the non-circular portion 262 is positioned within a range of 90 degrees from the reference surface B on the side close to the guide wire lumen 21 centering on the axis center O2 of the imaging core lumen 26.

Moreover, the sheath distal portion 21 partially includes a support portion 263 having an inner diameter r equal to that of the circular portion 261 in at least a part of the side close to the guide wire lumen 211. In the exemplary embodiment, the support portion 263 is positioned on the reference surface B. Since the support portion 263 having the inner diameter r equal to that of the circular portion 261 is provided, the ultrasound transducer 411 (observation unit) and the rotary shaft 42 can be stably supported during rotation, and thus, a favorable image can be acquired.

An inner surface 262A and an outer surface 262B of the non-circular portion 262, respectively defining parts of the inner circumferential surface and the outer circumferential surface of the sheath distal portion 21, are formed so as to be planes. Particularly, the outer surface 262B of the non-circular portion 262 is formed so as to connect the tangential line of the outer surface of a portion where the guide wire lumen 211 of the sheath distal portion 21 is formed and the tangential line of the outer surface of a portion where the imaging core lumen 26 is formed. Therefore, the sheath distal portion 21 can have high strength while being minimized in size as much as possible. In addition no recessed portion in which blood and the like may accumulate is formed between the portion where the guide wire lumen 211 of the sheath distal portion 21 is formed aid the portion where the imaging core lumen 26 is formed.

In addition, the thickness of the non-circular portion 262 is constant from the imaging core lumen 26 side to the guide wire lumen 211 side.

The sheath distal portion 21 is formed of a material having properties of highly transmitting ultrasound waves. The sheath distal portion 21 is formed of a flexible material, and the material is not particularly limited. For example, various types of thermoplastic elastomers such as a styrene-based elastomer, a polyolefin-based elastomer, a polyurethane-based elastomer, a polyester-based elastomer, a polyamide-based elastomer a polyimide-based elastomer, a polybutadiene-based elastomer, a trans-polyisoprene-based elastomer, a fluorine rubber-based elastomer, and a chlorinated polyethylene-based elastomer can be exemplified. One type, or a combination of two types or more (a polymer alloy, a polymer blend, a stacked body, and the like) among thereof can also be adopted.

The sheath main body portion 22 is positioned on the proximal side closer than the sheath distal portion, and the imaging core lumen 26 is formed inside the sheath main body portion 22. The sheath main body portion 22 is formed of a flexible materials and the material is not particularly limited. For example, the sheath a body portion 22 is formed of a material similar to that of the above-described sheath distal portion 21.

For example the sheath distal portion 21 in which the imaging core lumen 26 and the guide wire lumen 211 are formed side by side can be molded through extrusion mold ing, heat-welding, or the like.

Figure 5:
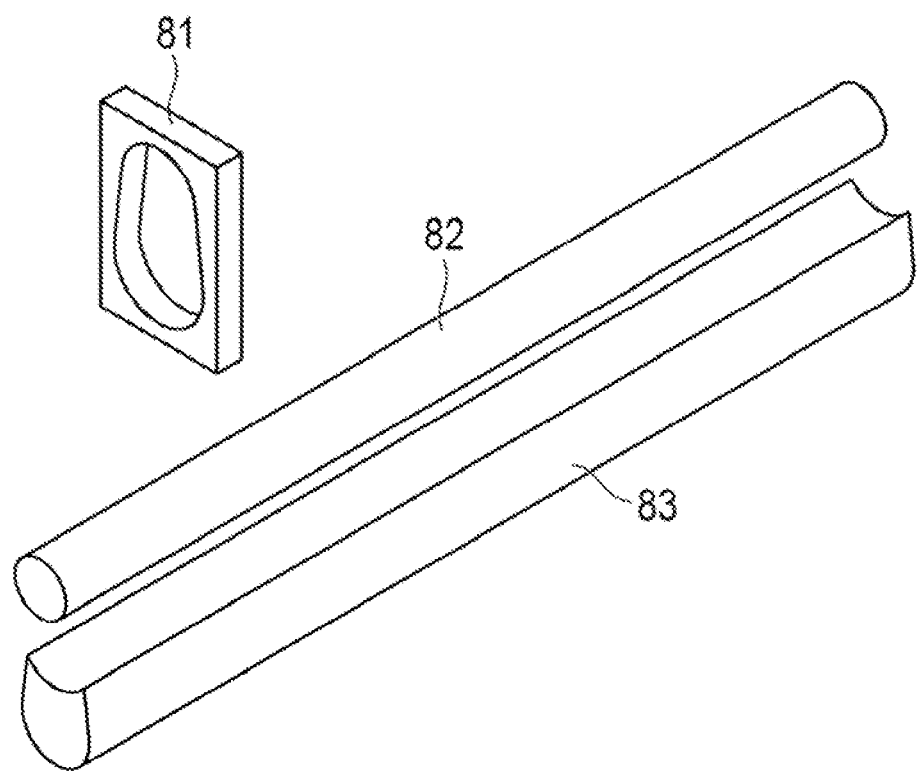
FIG. 5 is a perspective view illustrating a part of an instrument for molding a sheath distal portion.

In case where the sheath distal portion 21 is molded through extrusion molding, as illustrated in FIG. 5, the guide wire lumen 211 and the imaging core lumen 26 can be molded at the same time by adopting an extrusion die 81 for regulating the shape of the outer circumferential surface of the sheath distal portion 21, a first core bar 82, and a second core bar 83. The first core bar 82 regulates the shape of the guide wire lumen 211, and the second core bar 83 regulates the shape of the imaging core lumen 26.

Figure 6:
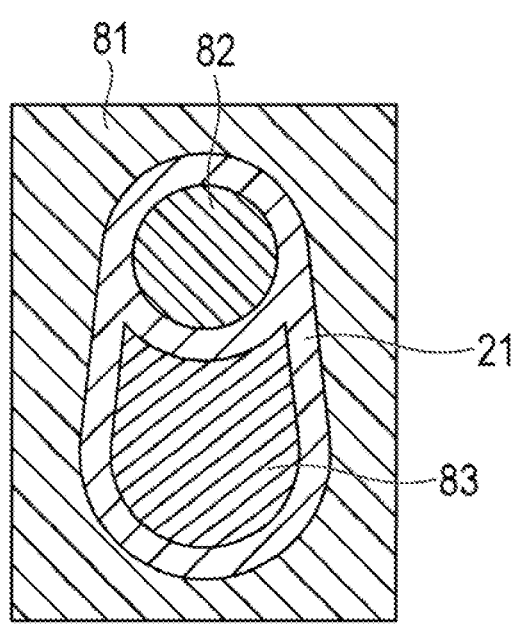
FIG. 6 is a cross-sectional view for describing a state where the sheath distal portion is molded through extrusion molding.

When extrusion molding is performed, the first core bar 82 and the second core bar 83 have shapes different from each other so as to correspond to the shapes of the imaging core lumen 26 and the guide wire lumen 211. As illustrated in FIG. 6, a material which has been subjected to heating and melting and is extruded out from an extruder fills the area surrounding the first core bar 82 and the second core bar 83. The first core bar 82 and the second core bar 83 are moved in the axial line direction by a retractor and pass through the inside of the extrusion die 81, and the shape of the outer circumferential surface of the sheath distal portion 21 is regulated. After extrusion molding, the first core bar 82 and the second core bar 83 are evulsed from the material which has been cooled and hardened, and the sheath distal portion 21 is formed by performing a necessary process such as cutting.

In extrusion molding, the sheath distal portion 21 can be molded by adopting dies corresponding to the shape of the outer surface of the sheath distal portion 21, the shape of the inner surface of the imaging core lumen 26, and the shape of the inner surface of the guide wire lumen 211, without adopting the core bars.

Figure 7:
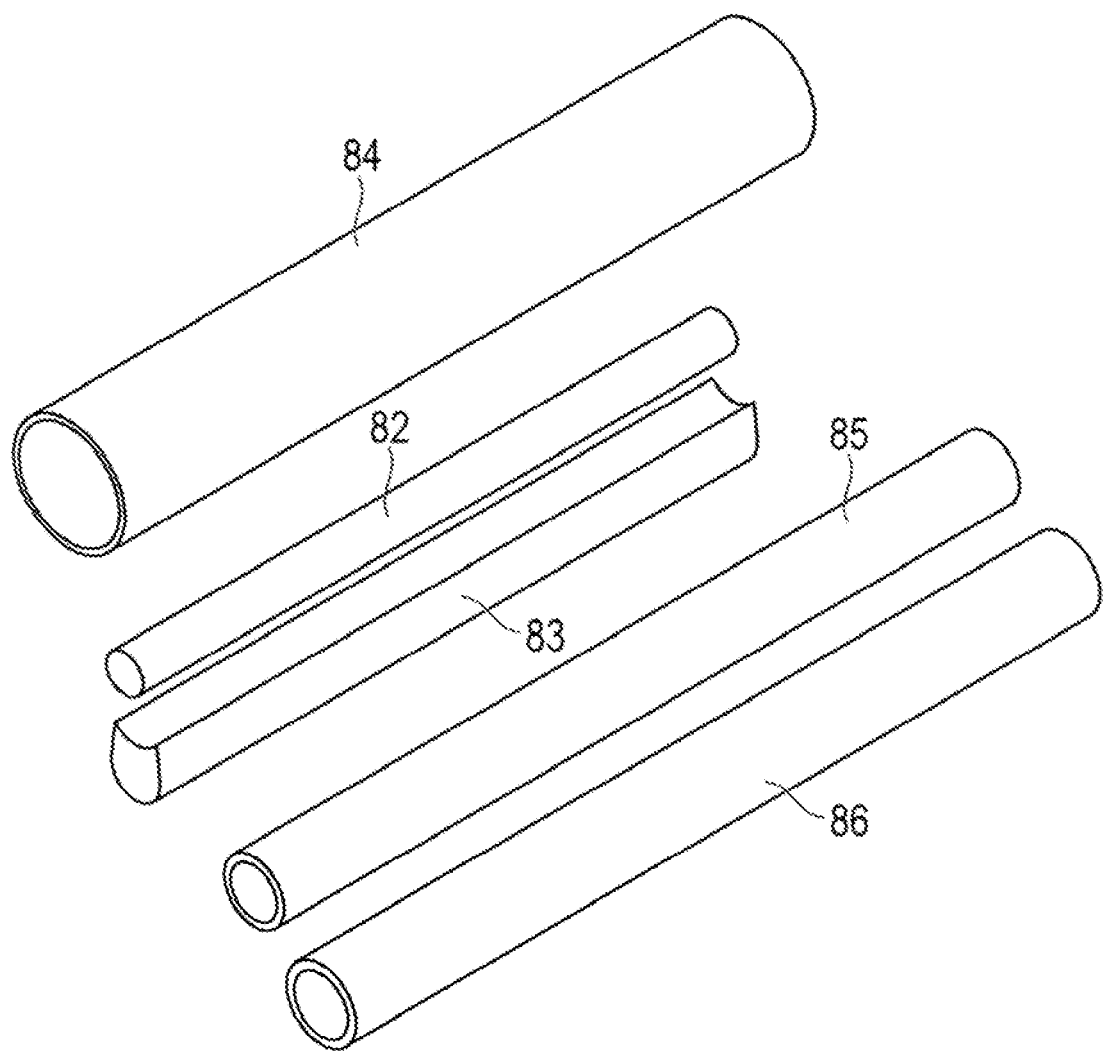
FIG. 7 is a perspective view illustrating a part of an instrument for molding the sheath distal portion through heat-welding, and materials.
Figure 8:
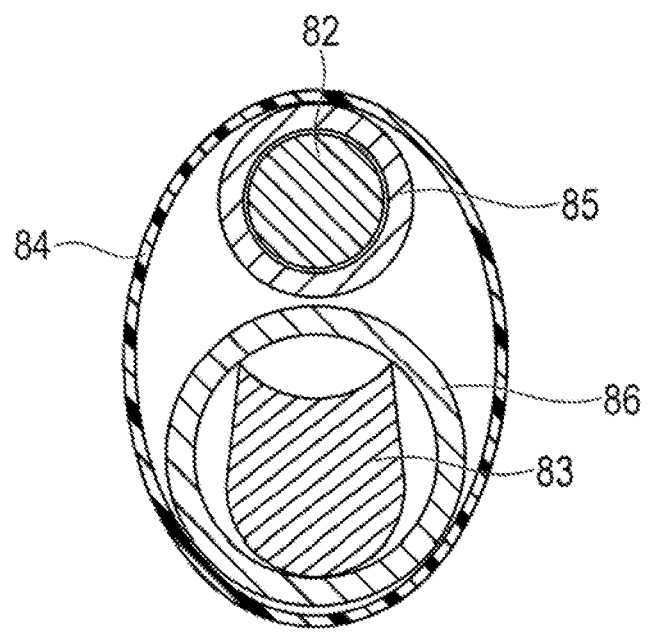
FIG. 8 is a cross-sectional view for describing a state where the sheath distal portion is molded through heat-welding.
Figure 9:
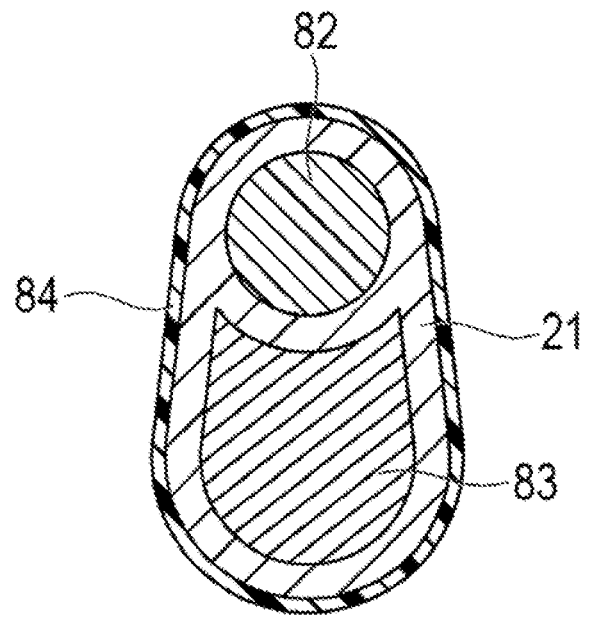
FIG. 9 is a cross-sectional view for describing another state where the sheath distal portion is molded through heat-welding.

In a case where the sheath distal portion 21 is molded through the as illustrated in FIG. 7, a first tube 85 for forming the guide wire lumen 211, and a second tube 86 for forming the imaging core lumen 26 are prepared. Moreover, the first core bar 82 and the second core bar 83 having shapes different from each other so as to correspond to the shapes of the imaging core lumen 26 and the guide wire lumen 211 are manufactured. Subsequently, the first tube 85 having the first core bar 82 inserted therein and the second tube 86 having the second core bar 83 inserted therein are inserted into one heat-contraction tube 84. Thereafter, when heating is performed by using a heat source such as a heater, the first tube 85 and the second tube 86 are softened through the heating and are pressed against each other due to the contraction force of the heat-contraction tube 84 which contracts through the heating, thereby integrating the first tube 85 and the second tube 86 together. Thereafter, the heat-contraction tube 84 is removed from the material which has been cooled and hardened, and the first core bar 82 and the second core bar 83 are evulsed. Then, the sheath distal portion 21 is formed by performing a necessary process such as cutting.

As illustrated in FIG. 3, in the filling liquid in-out path member 23, a priming port 231 is formed as a hole through which a physiological salt solution filling the inside of the sheath 2 flows out so as to communicate with the imaging core lumen 26 inside the sheath 2.

The rotary shaft 4 is flexible and also has characteristics in that rotary power generated by the operation unit 3 (refer to FIG. 1) can be transmitted to the transducer unit 41. For example, the rotary shaft 42 is configured to be a pipe body having a multi-layer coil shape such as a three-layer coil in which winding directions are alternately arranged in a right-left-right manner. When the rotary shaft 42 transmits rotary power, the transducer unit 41 rotates, and thus, a target lesion inside a lumen such as a blood vessel and the vessel, can be observed in the circumferential direction. In addition, a signal line 54 for transmitting a signal detected by the transducer unit 41 to the operation unit 3 passes through the inside of the rotary shaft 42.

As illustrated in FIG. 1, the operation unit 3 includes a hub 31 having a port 311 through which a physiological salt solution for air-bleeding is injected, a unit connector 37 which is connected to the hub 31 via an inner tube 34, and a relay connector 33 which is connected to the unit connector 37 via an outer tube 32 and which connects the sheath 2 and the operation unit 3 together.

The hub 31 holds the rotary shaft 42 and the inner tube 34. When the inner tube 34 is thrust into or is drawn out from the unit connector 37 and the outer tube 32, the rotary shaft 42 slides inside the sheath 2 in the axial line direction in association therewith.

When the inner tube 34 is maximally thrust, as illustrated in FIG. 1, the end portion of the inner tube 34 on the sheath side arrives at a location near the sheath side end portion of the outer tube 32, that is, a location near the relay connector 33. In this state, the transducer unit 41 is positioned near the distal end of the sheath 2.

Figure 10:
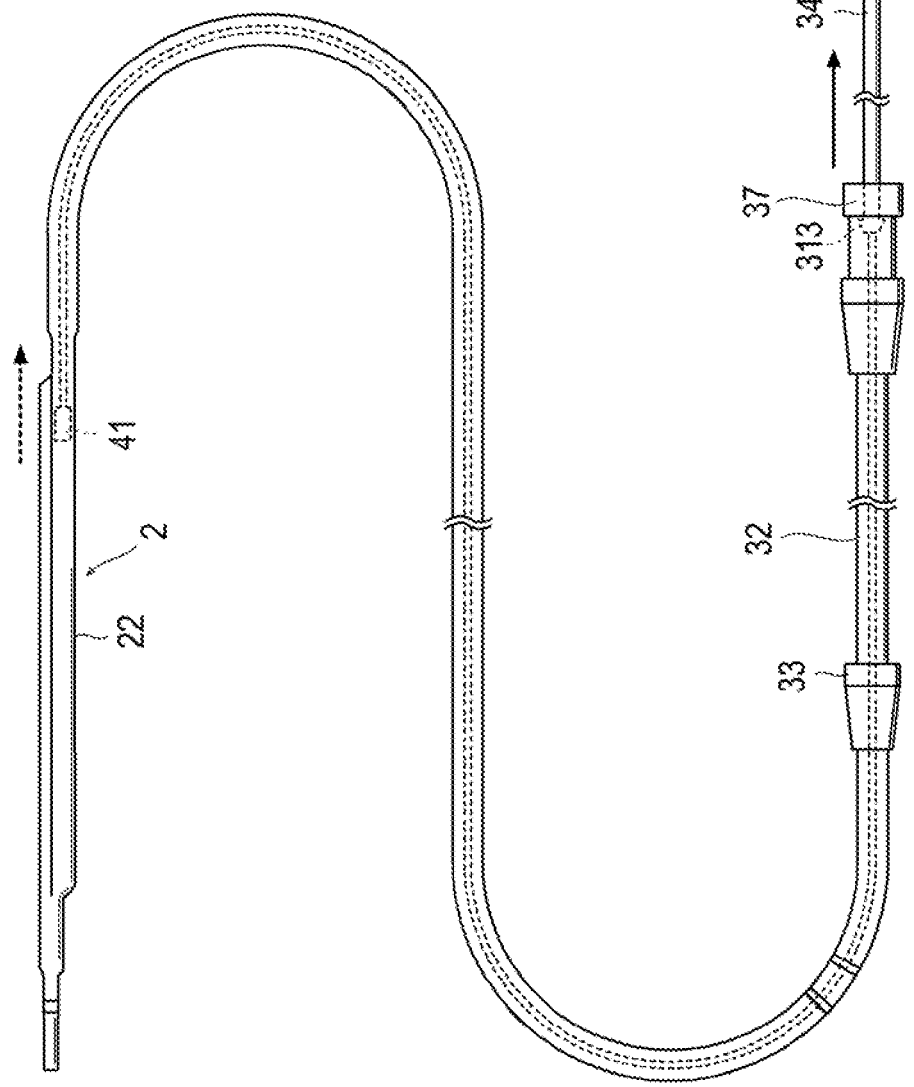
FIG. 10 is a plan view illustrating the medical device when a transducer unit is pulled back.

In addition, when the inner tube 34 is maximally drawn out, as illustrated in FIG. 10, a stopper 313 formed at the distal end is caught by the inner wall of the unit connector 37 so that the inner tube 34 other than the portion near the caught distal end is exposed. In this state, the transducer unit 41 is caused to return (withdraw) through the inside of the lumen while the sheath 2 is left behind. When the transducer unit 41 moves while rotating, a tomographic image of a blood vessel and the like can be produced.

Figure 11:
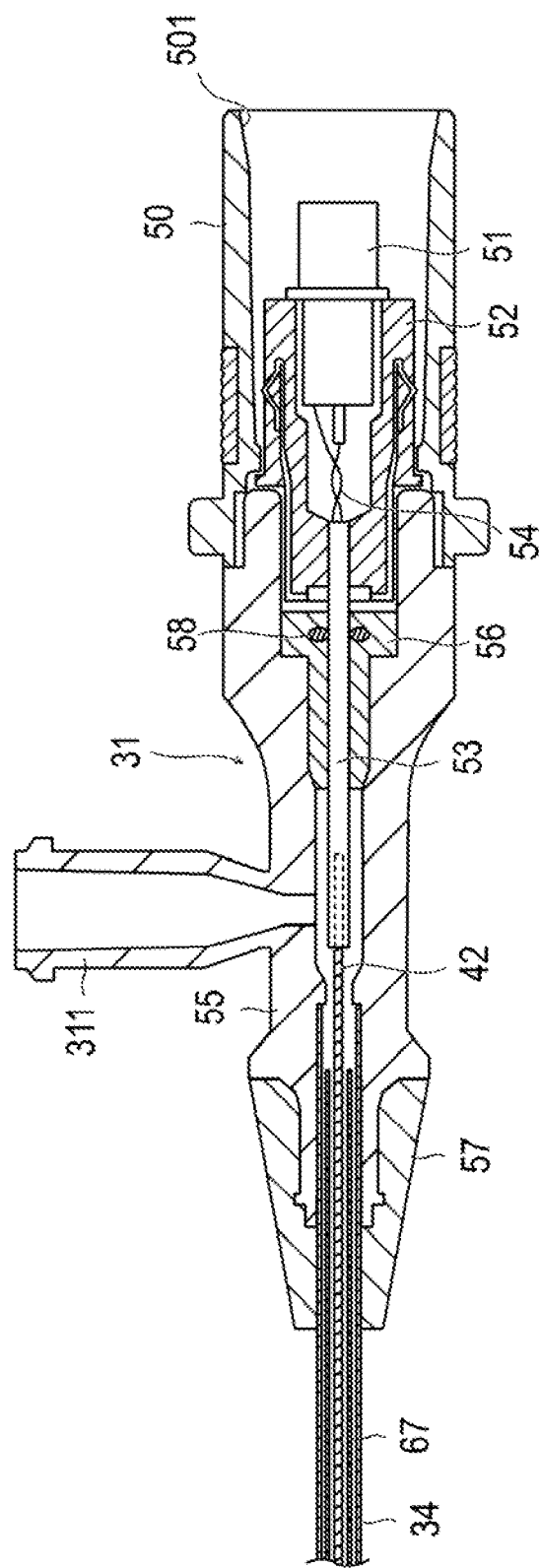
FIG. 11 is a cross-sectional view in a longitudinal direction illustrating a hub of the medical device.

As illustrated in FIG. 11, the hub 31 of the operation unit 3 has a joint 50, a male connector 51, a rotor 52, a connection pipe 53, the signal line 54, a hub main body 55, a seal member 56, and an anti-kink protector 57.

The joint 50 has an opening portion 501 on a user's hand-side of the ultrasound catheter 1, and the male connector 51 and the rotor 52 are disposed inside the joint 50. The male connector 51 can be interlocked with a female connector 711 (refer to FIG. 2) included in the external drive apparatus 7, from the opening portion 501 side of the joint 50. Accordingly, the external drive apparatus 7 and the male connector 51 are mechanically and electrically interlocked with each other.

The rotor 52 non-rotatably holds the connection pipe 53 and rotates integrally with the male connector 51. In order to transmit rotations of the rotor 52 to the rotary shaft 42, the connection pipe 53 holds the rotary shaft 42 at the end portion opposite to the rotor 52 side. The signal line 54 passes through the inside of the connection pipe 53. One end of the signal line 54 is connected to the male connector 51, and the other end passes through the inside of the rotary shaft 42 and is connected to the transducer unit 41. An observation result obtained by the transducer unit 41 is transmitted to the external drive apparatus 7 via the male connector 51. The observation result is subjected to suitable processing and is displayed as an image.

In the hub main body 55, a physiological salt solution is injected through the port 311, and the physiological salt solution is introduced into the inner tube 34 without leaking out. The seal member 56 including an O-ring 58 is installed between the hub main body 55 and the joint 50. Accordingly, the physiological salt solution does not leak to the opening portion 501 side of the joint 50.

The proximal portion of the inner tube 34 is inserted into the hub main body 55 such that the outer circumferential surface of the inner tube 34 is fitted to an inner circumferential surface 551 inside thereof. The anti-kink protector 57 is disposed around the inner tube 34 and the hub main body 55.

Figure 12:
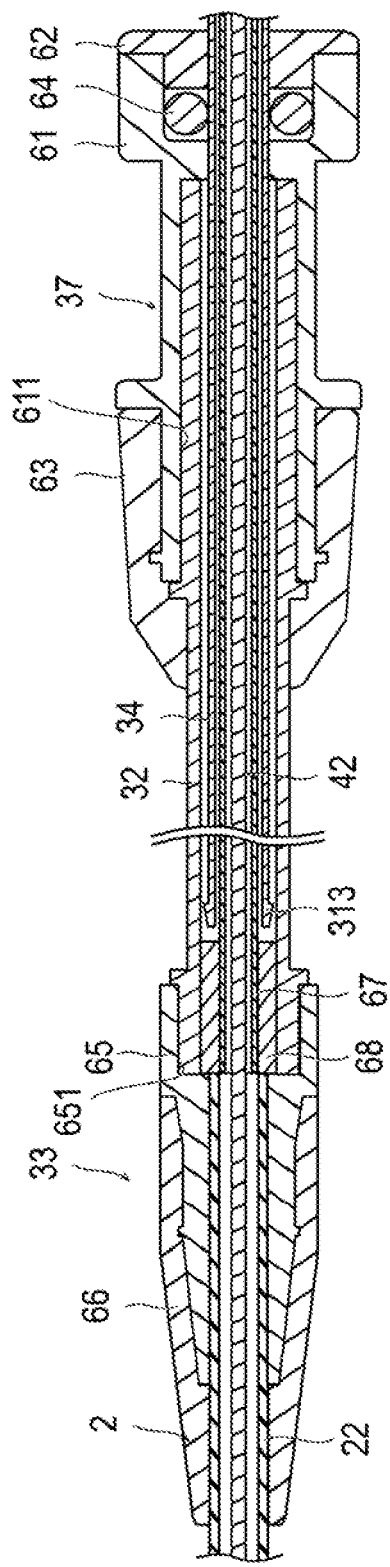
FIG. 12 is a cross-sectional view in the longitudinal direction illustrating a unit connector and a relay connector of the medical device.

As illustrated in FIG. 12, the unit connector 37 has a unit connector main body 61, a sealing member 62, a cover member 63, and a washer 64.

The unit connector main body 61 is inserted such that the proximal portion of the outer tube 32 attached to the relay connector 33 is fitted to an inner circumferential surface 611 inside thereof, and the inner tube 34 extending from the hub 31 is inserted into the outer tube 32. The sealing member 62 is combined with the unit connector main body 61 and holds the washer 64. The cover member 63 is combined with the unit connector main body 61 and holds the outer tube 32. The washer 64 seals a space between the unit connector main body 61 and the sealing member 62. Accordingly, even though a physiological salt solution supplied through the port 311 of the hub 31 passes through the inner tube 34 and flows into the outer tube 32, the physiological salt solution does not leak out from the unit connector 37.

In addition, since the stopper 313 is formed at the distal end of the inner tube 34 extending from the hub 31, even when the hub 31 is maximally pulled, that is, even when the inner tube 34 is maximally drawn out from the outer tube 32, the stopper 313 is caught by the inner wall of the unit connector main body 61 so that the inner tube 34 is not drawn out from the unit connector 37.

The relay connector 33 has an outer tube holding portion 65 and an anti-kink protector 66. A part of the outer tube 32 is inserted into the outer tube holding portion 65 such that the outer circumferential surface of the distal portion of the outer tube 32 is fitted to an inner circumferential surface 651 inside thereof. In addition, the proximal side end portion of the sheath main body portion 22 is interlocked with the inner circumferential surface 651 of the outer tube holding portion 65, and a path guiding the rotary shaft 42 which has passed through the outer tube 32, and a physiological salt solution to the sheath 2 is formed on the inner circumferential surface 651. In FIG. 12, the sheath main body portion 22 has a one-layer structure, however, a multi-layer structure may also be applied.

A spacer tube 68 through which the rotary shaft 42 passes is disposed inside the distal portion of the outer tube 32 fitted to the outer tube holding portion 65, and a protection tube 67 is fixed to the inner wall of the spacer tube 68. The protection tube 67 extends toward the inside of the inner tube 34 extending from the hub 31 and is disposed between the rotary shaft 42 and the inner tube 34. Therefore, when the inner tube 34 is thrust into the outer tube 32, the protection tube 67 is thrust into the inner tube 34 in a direction opposite to the thrusting direction. When the inner tube 34 is thrust into or drawn out from the outer tube 32, the protection tube 87 is relatively thrust into or pulled out from the inner tube 34 in the opposite direction as well. Therefore, even though warping force may be generated in the rotary shaft 42 due to friction caused by contact with the inner tube 34, the warping force is suppressed by the protection tube 67, and thus, bending and the like can be prevented. The protection tube 67 is formed of a metal pipe body having a rough-winding coil shape. Therefore, a physiological salt solution can flow through gaps of the coil, and thus, no air remains inside the outer tube 32.

The configuration materials of the outer tube 32, the inner tube 34, the spacer tube 68, the hub 31, the unit connector main body 61, and the outer tube holding portion 65 are not particularly limited. For example, it is possible to exemplify various resins such as polyvinyl chloride, polyethylene, polypropylene, cyclic polyolefin, polystyrene, poly-(4-methylpentene-1), polycarbonate, an acrylic resin, an acrylonitrile-butadiene-styrene copolymer, polyester such as polyethylene terephthalate and polyethylene naphthalate, a butadiene-styrene copolymer, and polyamide (for example, nylon 6, nylon 6.6, nylon 6.10, and nylon 12). Note that, the configuration materials of the members are appropriately selected in accordance with the required function. Therefore, the members can be formed of materials different, from each other.

As illustrated in FIG. 2, the above-described ultrasound catheter 1 is connected, to the external drive apparatus 7 and is thereby driven. On a base 75, the external drive apparatus 7 is provided with a drive unit 71 which is internally equipped with an external drive source such as a motor and rotationally drives the rotary shaft 42, movement means 72 which holds the drive unit 71 and moves the drive unit 71 in the axial line direction by a motor or the like, and a holding portion 73 which holds a part of the ultrasound catheter 1 in a positionally fixed manner. The external drive apparatus 7 is connected to a control unit 79 controlling the drive unit 71 and the movement means 72, and a display unit 78 connected to the control unit 79 displays an image obtained through the transducer unit 41.

The movement means 72 is a feed mechanism in which the drive unit 71 can be held and fixed and the held drive unit 71 is moved forward and rearward along a groove rail 76 on the base 75.

The drive unit 71 has the driving female connector 711 to which the driving male connector 51 of the ultrasound catheter 1 can be connected, and a joint connection section 712 which can be connected to the joint 50 of the ultrasound catheter 1. At the same time a signal can be transmitted and received with respect to the transducer unit 41 due to the connection, the rotary shaft 42 can be rotated.

Ultrasound scanning in the ultrasound catheter 1 is performed by transmitting rotary motion of the motor inside the drive unit 71 to the rotary shaft 42, rotating the housing 412 fixed to the distal end of the rotary shaft 42, and performing scanning of ultrasound waves transmitted and received through the ultrasound transducer 411 provided in the housing 412, in a substantially radial direction. In addition, the ultrasound catheter 1 in its entirety is pulled toward the proximal side, and the ultrasound transducer 411 is moved in the longitudinal direction. Accordingly, a cross-sectional image of surrounding tissue in the axial line direction inside a blood vessel can be obtained by performing scanning to an arbitrary position.

A description will now be given regarding an operation in which biological tissue is observed inside a biological lumen such as a blood vessel by adopting the ultrasound catheter 1 according to the exemplary embodiment.

First, before the sheath 2 of the ultrasound catheter 1 is inserted into a lumen, a priming operation of filling the inside of the ultrasound catheter 1 with a physiological salt solution is performed. When the priming operation is performed, ultrasound waves can be transmitted from the ultrasound transducer 411, air inside the ultrasound catheter 1 is eliminated, and air is prevented from entering the inside of the lumen such as a blood vessel.

In order to perform the priming, the hub 31 is caused to be in a state of being maximally pulled from the unit connector 37 to the user's hand-side, that is, a state where the inner tube 34 is maximally drawn out from the outer tube 32 (refer to FIG. 10), and a physiological salt solution is injected by using an injection syringe, for example, via instruments including a tube and a three-way stopcock (not illustrated) connected to the port 311 of the hub 31. The injected physiological salt solution fills the entire inside of the sheath 2 from the hub 31 to the distal end. When the inside of the ultrasound catheter 1 is completely filled with the physiological salt solution, the physiological salt solution is discharged from the priming port 231 formed in the filling liquid in-out path member 23 (refer to FIG. 3) of the sheath 2. Accordingly, the filling state of the physiological salt solution is checked. By performing the priming operation, air inside the ultrasound catheter 1 can be eliminated, and air can be prevented from entering the inside of the lumen.

During priming, since the sheath distal portion 21 is provided with the non-circular portion 262 having the significant inner diameter r of the imaging core lumen 26 the volume inside the imaging core lumen 26 increases, and thus the physiological salt solution can replace the inside thereof at low pressure.

Subsequently, as illustrated in FIG. 2, the ultrasound catheter 1 is interlocked with the external drive apparatus 7 covered with a sterilized polyethylene bag (not illustrated). In other words, the joint 50 (refer to FIG. 11) of the hub 31 of the ultrasound catheter 1 is connected to the joint connection section 712 of the drive unit 71. Accordingly, the rotary shaft 42 can be rotated at the same time a signal can be transmitted and received between the transducer unit 41 and the external drive apparatus 7. When the unit connector 37 is fitted to the holding portion 73, interlocking is completed.

Subsequently, by moving the drive unit 71 to the distal side along the groove rail 76 on the base 75, the hub 31 is thrust toward the distal side, and the inner tube 34 is in a state of being maximally thrust into the outer tube 32 (refer to FIG. 1).

Subsequently, the guide wire 25 is inserted into a biological lumen such that the distal portion thereof arrives at a location near a target position to be observed. Thereafter, the proximal portion of the guide wire 25 is inserted through the distal end opening portion of the guide wire lumen 211 of the ultrasound catheter 1, and the ultrasound transducer 411 is disposed on an inner side (distal side) closer than the target lesion to be observed by moving the sheath 2 along the guide wire 25. In this state, as illustrated in FIG. 10, the sheath 2 is held so as not to move, and a pull-back operation is performed while the rotary shaft 42 is rotated by the drive unit 71. Accordingly, the ultrasound transducer 411 is moved in the axial line direction toward the proximal side closer than the target lesion while performing radial scanning, and thus, an image of biological tissue including the target lesion can be acquired along the axial line direction of the lumen.

The pull-back operation can be performed by causing the control unit 79 to operate the movement means 72 connected to the rear end portion of the ultrasound catheter 1. After the control unit 79 performs digital processing of the acquired data, the display unit 7 displays the processed data as image data.

Figure 13:
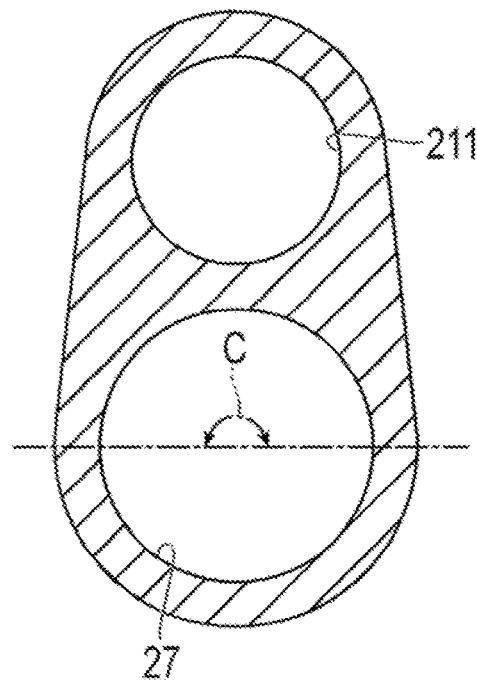
FIG. 13 is a cross-sectional view illustrating a comparative example of the sheath distal portion.

When an image is acquired, since the non-circular portion 262 is formed in the sheath distal portion 21 and the thickness of the catheter wall at the non-circular portion 262 is thin (i.e., remains constant), a missing image occurring due to attenuation of an ultrasound wave, light, and the like can be reduced as much as possible. In contrast, as in the comparative example illustrated in FIG. 13, in a case where the inner diameters of an imaging core lumen 27 are constant in all the circumferential directions, thick portions are generated on the side close to the guide wire lumen 211 of the imaging core lumen 27, and attenuation of an ultrasound wave increases in a range C of substantially 180 degrees on the side close to the guide wire lumen 211. Thus, a missing image easily occurs. Thus, in the exemplary embodiment, as illustrated in FIG. 4, since the non-circular portion 262 having distances from the axis center O2 to the inner surface of the imaging core lumen 27 longer than the circular portion 261 is formed, attenuation of an ultrasound wave is reduced, and an angle θ at which a missing image easily occurs even though the guide wire lumen 211 is formed can be reduced. Therefore, an image can be favorably acquired throughout a wide range. The angle θ is regulated by a partition wall between the imaging core lumen 26 and the guide wire lumen 211 and can be appropriately set in accordance with the size of the imaging core lumen 26 or the guide wire lumen 211. For example, the angle θ is approximately 60 degrees.

In addition, the sheath distal portion 21 partially includes a support portion 263 having the inner diameter r equal to that of the circular portion 261 in at least a part of the side close to the guide wire lumen 211. Therefore, the ultrasound transducer 411 (observation unit) and the rotary shaft 42 can be stably supported during rotation, and thus, a favorable image can be acquired.

In addition, since the wall thickness of the non-circular portion 262 is constant toward the guide wire lumen 211 side, attenuation of an ultrasound wave in the non-circular portion 262 can be easily anticipated. Thus, an acquired image can be easily corrected.

In addition, since the outer surface 262B configuring the outside of the non-circular portion 262 is formed so as to be a planar surface on the outer circumferential surface of the sheath 2 (pipe body), high strength can be obtained while the sheath 2 is minimized in size as much as possible, and blood and the like are unlikely to be accumulated compared to a case where the recessed portion is formed on the outer circumferential surface. Thus, a thrombus and the like can be suppressed from adhering thereto.

Thereafter, a pull-forward operation is performed while the rotary shaft 42 is rotated by the drive unit 71, and the ultrasound transducer 411 is moved inside the imaging core lumen 26 in the distal direction so as to return to the original state (refer to FIG. 1). Thereafter, the ultrasound catheter 1 is evulsed from the inside of the blood vessel, and the operation of the ultrasound catheter 1 is completed.

The disclosure herein is not limited to only the above-described embodiment, and various changes can be made by those skilled in the art within the scope of the technical concept of the invention. For example, in the above-described embodiment, description has been given regarding a case where the disclosure is applied to an ultrasound catheter. However, the disclosure can, also be applied to an apparatus which acquires an image by utilizing light, such as an optical coherence tomography (OCT) diagnostic apparatus and an optical frequency domain imaging (OFDI) diagnostic apparatus.

Figure 14:
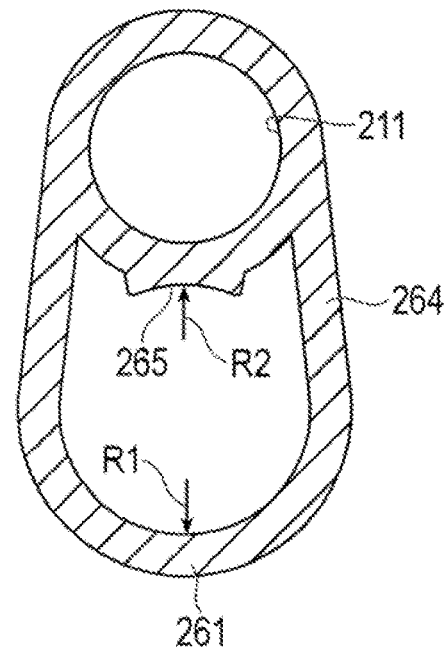
FIG. 14 is a cross-sectional view illustrating a modified example of the sheath distal portion.

In addition, as in the modified example illustrated in FIG. 14, a support portion 265 provided together with a non-circular portion 264 on the side close to the guide wire lumen 211 may have curvature R2 equal to curvature R1 of the circular portion 261. In this manner, the ultrasound transducer 411 and the rotary shaft 42 can be more stably supported during rotation, and thus, a favorable image can be acquired.

Figure 15:
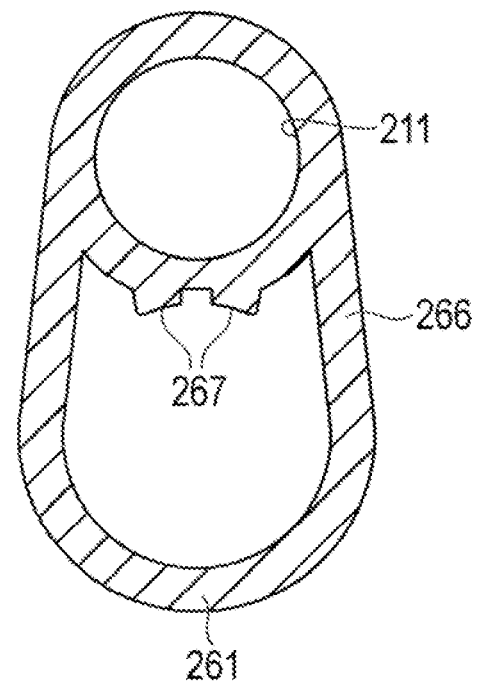
FIG. 15 is a cross-sectional view illustrating another modified example of the sheath distal portion.

In addition, as in another modified example illustrated in FIG. 15, a plurality of support portions 267 together with a non-circular portion 266 may be provided on the side close to the guide wire lumen 211.

Figure 16:
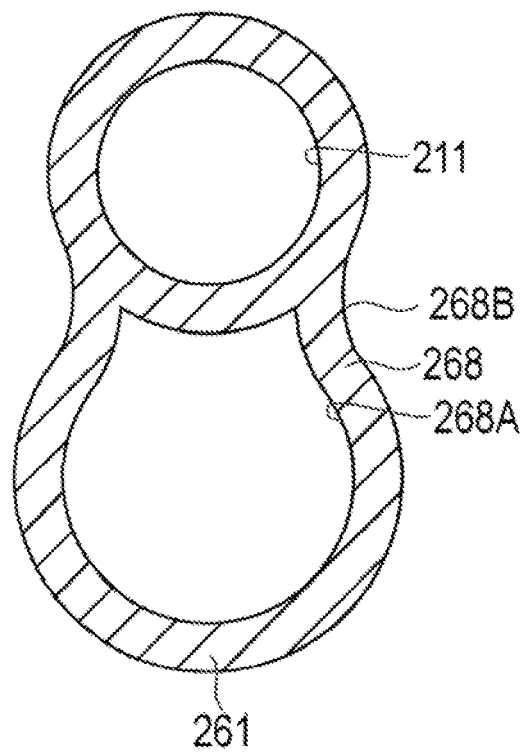
FIG. 16 is a cross-sectional view illustrating a further modified example of the sheath distal portion.

In addition, as in a further modified example illustrated in FIG. 16, an inner surface 268A and an outer surface 268B of a non-circular portion 268 do not have to be planar surfaces.

Figure 17:
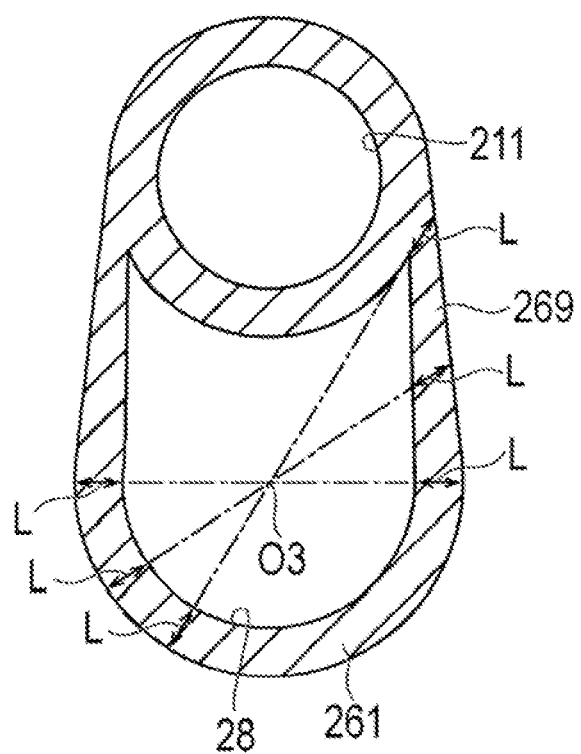
FIG. 17 is a cross-sectional view illustrating still another modified example of the sheath distal portion.

In addition, as in still another modified example illustrated in FIG. 17, the thickness of a non-circular portion 269 may be formed so as to be thinner toward the guide wire lumen 211 side. Particularly, it is preferable to set the thickness of the non-circular portion 269 such that lengths L of the non-circular portion 269 along the radiation direction centering on an axis center O3 of an imaging core lumen 28 become constant. In this manner, attenuation of an ultrasound wave and light in the non-circular portion 269 becomes approximately the same, as that in the circular portion 261. Thus an acquired image can be easily corrected.

In addition, in the medical device according to the above-described exemplary embodiment, there is provided only one guide wire lumen 211. However, two (or plurality of) divided guide wire lumens 211 may be provided in the axial line direction.

In addition, the medical device according to the above-described exemplary embodiment is a rapid exchange-type catheter in which the guide wire lumen 211 is formed in only the distal portion of the catheter. However, the medical device may be an over-the-wire-type catheter in which a guide wire lumen is formed throughout the entire catheter in the axial line direction.

The detailed description above describes a medical device. The invention is not limited, however, to the precise embodiments and variations described. Various changes, modifications and equivalents could be effected therein by one skilled in the art without departing from the spirit or scope of the disclosure as defined by the appended claims, it is expressly intended that all such changes, modifications and equivalents which fall within the scope of the claims are embraced by the claims.

What is claimed is:

1. A medical device comprising:
a tubular body that extends in a longitudinal direction and that includes both a guide wire lumen configured to allow a guide wire to be inserted therein and an imaging core lumen;
an imaging core insertable into the imaging core lumen to acquire image information inside a living body;
the imaging core including a transducer unit configured to be inserted into the imaging core lumen and a rotary shaft connected to the transducer unit, the rotary shaft being configureed to be inserted into the imaging core lumen and behind rotatable in order to transmit mechanical drive force to the imaging core;
the guide wire lumen and the imaging core lumen each having a cross-sectional shape as seen in a cross-section orthogonal to the longitudinal direction of the tubular body, the cross-sectional shape of the guide wire lumen and the cross-sectional shape of the imaging core lumen being different from one another,
the imaging core lumen of the tubular body, as seen in a cross-section orthogonal to the longitudinal direction of the tubular body, having a fixed cross-sectional area and including a circular portion and a non-circular portion, the circular portion of the imaging core lumen being positioned farther from the guide wire lumen than the non-circular portion of the imaging core lumen, the circular portion of the imaging core lumen having a uniform radii of curvature, and the non-circular portion of the imaging core lumen having an inner surface and distances from a center point of the circular portion of the imaging core lumen to the inner surface of the imaging core lumen being non-uniform and longer than the radius of the circular portion in at least a part of a side close to the guide wire lumen;
the tubular body that includes both the guide wire lumen and the imaging core lumen being a one-piece unitary tubular body as seen in the cross-section;
the tubular body having an outer circumferential surface, the outer circumferential surface of a portion of the tubular body surrounding the non-circular portion of the imaging core lumen being planar; and a thickness of the portion of the tubular body surrounding the non-circular portion of the imaging core lumen being constant.

2. The medical device according to claim 1, wherein the tubular body has a support portion having an inner diameter equal to the inner diameter of the circular portion in at least a part of the side close to the guide wire lumen.

3. The medical device according to claim 2, wherein the support portion has a radius of curvature equal to the radius of curvature of the circular portion.

4. The medical device according to claim 1, wherein the imaging core is an ultrasound transducer.

5. The medical device according to claim 1, wherein the imaging core lumen is non-symmetrical about a first line that passes through the center point of the circular portion of the imaging core lumen and that is perpendicular to a second line passing though both the center point of the circular portion of the imaging core lumen and a center of the guide wire lumen.

6. The medical device according to claim 1, further comprising a filling member positioned in the imaging core lumen at the distal end of the imaging core lumen and a port passing through the filling member to communicate the imaging core lumen with an exterior of the catheter, the port having an inner diameter smaller than an inner diameter of the imaging core lumen and smaller than an outer diameter of the transducer unit.

7. A catheter comprising:
a sheath having a sheath distal portion that extends in a longitudinal direction and a sheath main body portion;
an imaging core lumen formed in the sheath distal portion;
a guide wire lumen formed in the sheath distal portion;
the guide wire lumen including an open distal end and an open proximal end so that during use of the medical devices the guide wire positioned in the guide wire lumen extends distally beyond the open distal end of the guide wire lumen and proximally beyond the open proximal end of the guide wire lumen, the imaging core lumen extending proximally beyond the open proximal end of the guide wire lumen,
the guide wire lumen and the imaging core lumen each having a cross-sectional shape as seen in a cross-section orthogonal to the longitudinal direction of the sheath distal portion, the cross-sectional shape of the guide wire lumen and the cross-sectional shape of the imaging core lumen being different from one another,
the imaging core lumen and the guide wire lumen being positioned side by side in the sheath distal portion with a wall positioned between and separating the imaging core lumen and the guide wire lumen from one another, the imaging core lumen in the sheath distal portion including, as seen in cross-section orthogonal to the longitudinal direction of the sheath distal portion, a circular portion and a non-circular portion that together cooperatively define an inner surface of the imaging core lumen;
the wall including a first surface facing the guide wire lumen and a second surface facing the imaging core lumen, the first surface of the wall always being a concave-shaped surface, the second surface of the wall always being a convex-shaped surface;
the sheath in which both the guide wire lumen and the imaging core lumen are formed being a one-piece unitary sheath as seen in the cross-section;
the sheath having an outer circumferential surface, the outer circumferential surface of a portion of the sheath surrounding the non-circular portion of the imaging core lumen being planar; and
a thickness of the portion of the sheath surrounding the non-circular portion of the imaging core lumen being constant.

8. The catheter according to claim 7, wherein the non-circular portion of the imaging core lumen is positioned between the guide wire lumen and the circular portion of the imaging core lumen.

9. The catheter according to claim 7, wherein the circular portion has a radius of curvature equal to that of the imaging core lumen.

10. The catheter according to claim 7, wherein the sheath distal portion further includes a support portion.

11. The catheter according to claim 10, wherein at least a portion of the support portion has an inner diameter equal to that of the circular portion.

12. The catheter according to claim 7, wherein the imaging core lumen is non-symmetrical about a first line that passes through the center point of the circular portion of the imaging core lumen and that is perpendicular to a second line passing though both the center point of the circular portion of the imaging core lumen and a center of the guide wire lumen.

13. A catheter comprising:
a sheath that includes a sheath distal portion and a sheath main body portion located proximal of the distal portion;
an imaging core lumen formed in the sheath distal portion and configured to receive an imaging core, the imaging core lumen possessing a distal-most end;
a guide wire lumen formed in the sheath distal portion and configured to receive a guide wire, the guide wire lumen possessing a distal-most end, the distal-most end of the guide wire lumen being positioned distal of the distal-most end of the imaging core lumen;
a filling member positioned in the imaging core lumen at a distal end portion of the imaging core lumen, the filling member preventing the imaging core, when the imaging core is positioned in the imaging core lumen, from being moved distally beyond the filling member;
the guide wire lumen and the imaging core lumen each having a cross-sectional shape as seen in a transverse cross-section orthogonal to a longitudinal direction of the tubular body, the cross-sectional shape of the guide wire lumen and the cross-sectional shape of the imaging core lumen being different from one another;
a portion of the imaging core lumen and a portion of the guide wire lumen axially overlapping one another so as to be positioned side-by-side one another in the sheath distal portion with a wall positioned between and separating the imaging core lumen and the guide wire lumen from one another, the imaging core lumen possessing an inner surface, a first circumferential portion of the inner surface of the imaging core lumen as seen in a transverse cross-section being a circular portion defined by a radius of curvature, and a second circumferential portion of the inner surface of the imaging core lumen as seen in the transverse cross-section being a non-circular portion, the second circumferential portion of the inner surface of the imaging core lumen being positioned between the guide wire lumen and the first circumferential portion of the inner surface of the imaging core lumen as seen in the transverse cross-section;
the wall including a first surface facing the guide wire lumen and a second surface facing the imaging core lumen, the first surface of the wall always being a concave-shaped surface, the second surface of the wall always being a convex-shaped surface;

the sheath in which both the guide wire lumen and the imaging core lumen are formed being a one-piece unitary sheath as seen in the transverse cross-section;

the sheath having an outer circumferential surface, the outer circumferential surface of a portion of sheath surrounding the non-circular portion of the imaging core lumen being planar; and a thickness of the portion of the sheath surrounding the non-circular portion of the imaging core lumen being constant.

14. The catheter according to claim 13, wherein the inner surface of the imaging core lumen is planar at the portion of the sheath that surrounds the non-circular portion of the imaging core lumen and that has a planar outer circumferential surface.

15. The catheter according to claim 13, wherein the circular portion has a center from which the radius of curvature is measured, straight line distances from each of a plurality of spaced apart locations on the second circumferential portion of the inner surface of the imaging core lumen to the center of the circular portion being greater than the radius of curvature.

16. The catheter according to claim 13, further comprising a port passing through the filling member to communicate the imaging core lumen with an exterior of the catheter, the port having an inner diameter smaller than an inner dimeter of the imaging core lumen.

* * * * *